(12) United States Patent
Griffith

(10) Patent No.: US 10,660,912 B2
(45) Date of Patent: May 26, 2020

(54) COMBINATION THERAPY FOR CANCER

(71) Applicant: NuCana plc, Edinburgh (GB)

(72) Inventor: Hugh Griffith, Edinburgh (GB)

(73) Assignee: NuCana plc, Edinburgh (GB)

( * ) Notice: Subject to any disclaimer, the term of this patent is extended or adjusted under 35 U.S.C. 154(b) by 0 days.

(21) Appl. No.: 15/753,237

(22) PCT Filed: Oct. 5, 2015

(86) PCT No.: PCT/GB2015/052902
§ 371 (c)(1),
(2) Date: Feb. 16, 2018

(87) PCT Pub. No.: WO2017/060661
PCT Pub. Date: Apr. 13, 2017

(65) Prior Publication Data
US 2018/0271889 A1 Sep. 27, 2018

(51) Int. Cl.
| | | |
|---|---|---|
| A61K 31/7068 | (2006.01) | |
| A61K 35/00 | (2006.01) | |
| A61K 9/00 | (2006.01) | |
| A61K 31/282 | (2006.01) | |
| A61P 35/00 | (2006.01) | |

(52) U.S. Cl.
CPC ........ *A61K 31/7068* (2013.01); *A61K 9/0019* (2013.01); *A61P 35/00* (2018.01); *A61K 31/282* (2013.01); *A61K 2300/00* (2013.01)

(58) Field of Classification Search
CPC ..... A61P 35/00; A61K 9/0019; A61K 31/282; A61K 31/7084; A61K 2300/00
See application file for complete search history.

(56) References Cited

U.S. PATENT DOCUMENTS

| | | | |
|---|---|---|---|
| 7,951,787 B2 | 5/2011 | McGuigan | |
| 9,834,577 B2 | 12/2017 | Dammalapati et al. | |
| 10,005,810 B2 | 6/2018 | McGuigan et al. | |
| 1,011,788 A1 | 11/2018 | Griffith et al. | |
| 2003/0109697 A1 | 6/2003 | Shepard et al. | |
| 2006/0142238 A1* | 6/2006 | McGuigan | C07H 19/10 514/49 |
| 2017/0107246 A1 | 4/2017 | Griffith et al. | |
| 2017/0226147 A1 | 8/2017 | Griffith | |
| 2018/0273575 A1 | 9/2018 | McGuigan et al. | |
| 2018/0289733 A1 | 10/2018 | Griffith et al. | |
| 2018/0362571 A1 | 12/2018 | Kotala et al. | |
| 2019/0022118 A1 | 1/2019 | Griffith et al. | |

FOREIGN PATENT DOCUMENTS

| | | |
|---|---|---|
| FR | 2954310 A1 | 6/2011 |
| WO | WO-03/068164 A2 | 8/2003 |
| WO | WO-2004/041203 A2 | 5/2004 |
| WO | WO-2005/012327 A2 | 2/2005 |
| WO | WO-2009/036099 A1 | 3/2009 |
| WO | WO-2011/123672 A1 | 10/2011 |
| WO | WO-2014/076490 A1 | 5/2014 |
| WO | WO-2015/081133 A2 | 6/2015 |
| WO | WO-2015/198058 A1 | 12/2015 |
| WO | WO-2015/198059 A1 | 12/2015 |
| WO | WO-2016/012781 A1 | 1/2016 |
| WO | WO-2016/055769 A1 | 4/2016 |
| WO | WO-2016/181093 A1 | 11/2016 |
| WO | WO-2017/060661 A1 | 4/2017 |
| WO | WO-2017/098252 A1 | 6/2017 |
| WO | WO-2017/109444 A1 | 6/2017 |
| WO | WO-2017/109485 A1 | 6/2017 |
| WO | WO-2017/109486 A1 | 6/2017 |

OTHER PUBLICATIONS

International Search Report and Written Opinion for International Application No. PCT/GB2004/003148 dated Jan. 20, 2005.
Blagden et al., "A first in human Phase I/II study of NUC-1031 in patients with advanced gynecological cancers," J Clin Oncol, 33(15 Suppl):2547 (2015).
du Bois et al., "Phase III trial of carboplatin plus paclitaxel with or without gemcitabine in first-line treatment of epithelial ovarian cancer," J Clin Oncol, 28(27):4162-4169 (2010).
International Search Report and Written Opinion for International Application No. PCT/GB2015/052902 dated Dec. 2, 2015.
Slusarczyk et al., "Application of ProTide technology to gemcitabine: a successful approach to overcome the key cancer resistance mechanisms leads to a new agent (NUC-1031) in clinical development," J Med Chem, 57(4):1531-1542 (2014).
Blagden et al., "Anti-tumour activity of a first-in-class agent NUC-1031 in patients with advanced cancer: results of a phase I study," BJC 119:815-822 (2018).
Brito et al., "Safety and Efficacy of Gemcitabine Plus Cisplatin Combination in Pretreated Metastatic Breast Cancer Patients," Med Oncol 29(1): 33-38 (2012).
Brown et al., "Combination of Gemcitabine and Cisplatin is Highly Active in Women with Endometrial Carcinoma," Cancer, 116: 4973-4979 (2010).
Caira, "Crystalline Polymorphism of Organic Compounds," Top Curr Chem, 198: 163-208 (1998).
Chew et al., "Phase II Studies of Gemcitabine and Cisplatin in Heavily and Minimally Pretreated Metastatic Breast Cancer," J Clin Oncol 27(13): 2163-2169 (2009).
Cho et al., "Efficient synthesis of Exo-N-carbamoyl nucleosides: Application to the Synthesis of Phosphoramidate Prodrugs," Organ Letts 14(10):2488-2491 (2012).
Cho et al., "Efficient synthesis of nucleoside aryloxy phosphoramidate prodrugs utilizing benzyloxycarbonyl protection," Tetrahedron, 67(30):5487-5493 (2011).

(Continued)

*Primary Examiner* — Lawrence E Crane
(74) *Attorney, Agent, or Firm* — Dana M. Gordon; Foley Hoag LLP

(57) ABSTRACT

Disclosed is a combination of gemcitabine-[phenyl-benzoxy-L-alaninyl)]-phosphate (chemical name: 2'-Deoxy-2', 2'-difluoro-D-cytidine-5'-O-[phenyl (benzoxy-L-alaninyl)] phosphate) (NUC-1031) and a platinum-based anticancer agent selected from carboplatin, dicycloplatin, oxaliplatin, satraplatin and nedaplatin. The combinations are useful in the treatment of cancer and particularly ovarian cancer.

15 Claims, 4 Drawing Sheets

(56) References Cited

OTHER PUBLICATIONS

Ciccolini et al., "Pharmacokinetics and pharmacogenetics of Gemcitabine as a mainstay in adult and pediatric oncology: an EORTC-PAMM perspective," Cancer Chemother Pharmacol 78:1-23 (2016).

Ghazaly et al., "Acelarin: A novel nucleotide analogue that overcomes the key cancer resistance mechanisms with poor survival," Retrieved from the internet: http://www.nucanabiomed.com/downloads/Nucana2014AACRPoster.pdf (2014).

Ghazaly et al., "ProGem1: A phase I/II study of a first-in-class nucleotide analogue(NUC-1031) in patients with advanced solid tumours," Retrieved from the internet:http://www.nucanabiomed.com/downloads/Nucana2014ASCOPoster.pdf (2014).

Ghazaly et al., "ProGem1: Phase I first-in-human study of the novel nucleotide analogue NUC1031 in adult patients with advanced solid tumours," 2013 Methods & Results (2013).

Imperial College Healthcare NHS Trust, 'Safety and Efficacy Study of NUC-1031 and Carboplatin Combination to Treat Recurrent Ovarian Cancer' Study NCT02303912 (2014).

International Search Report for International Application No. PCT/GB2013/053018 dated Dec. 20, 2013.

International Search Report for International Application No. PCT/GB2015/051438 dated Nov. 20, 2015.

International Search Report for International Application No. PCT/GB2015/052839 dated Jan. 27, 2016.

International Search Report for International Application No. PCT/GB2015/054158 dated Apr. 8, 2016.

International Search Report for International Application No. PCT/GB2018/052445 dated Nov. 22, 2018.

MACS—Miltenyi Biotec, "Cancer Stem Cells," Retrieved from the internet: https://www.miltenyibiotec.com/~/media/Images/Products/Import/0001700/1M0001784.ashx (2008).

McGuigan, "A phosphoramidate ProTide (NUC-1031) and acquired and intrinsic resistance to gemcitabine," J Clin Oncol, 29:E13540 (2011).

She et al., "Resistance of leukemic stem-like cells in AML cell line KG1a to natural killer cell-mediated cytotoxicity," Cancer Lett, 318(2):173-179 (2012).

The Christie NHS Foundation Trust, "ABC-08: Phase Ib Trial of Acelarin in Combination with Cisplatin in Locally Advanced/Metastic Biliary Tract Cancers (ABC-08)," Available from: https://clinicaltrials.gov/ct2/show/study/NCT02351765 NLM Identifier: NCT02351765 (2015).

UK Clinical Trial Gateway, "ABC-08: Phase Ib Trial of Acelarin in Combination with Cisplatin in Locally Advanced/Metastic Biliary Tract Cancers," NCT02351765 (2015).

Valle et al., "Cisplatin plus Gemcitabine versus Gemcitabine for Biliary Tract Cancer," NEJM 362(14): 1273-1281 (2010).

* cited by examiner

COMBINATION THERAPY FOR CANCER

RELATED APPLICATION

This application is a § 371 national-stage application based on Patent Cooperation Treaty Application serial number PCT/GB2015/052902, filed Oct. 5, 2015.

This invention relates to a combination of gemcitabine-[phenyl-benzoxy-L-alaninyl)]-phosphate (chemical name: 2'-Deoxy-2',2'-difluoro-D-cytidine-5'-O-[phenyl (benzoxy-L-alaninyl)] phosphate) (NUC-1031) and a platinum-based anticancer agent selected from carboplatin, dicycloplatin, oxaliplatin, satraplatin and nedaplatin.

BACKGROUND

NUC-1031

Gemcitabine (1; marketed as Gemzar®) is an effective nucleoside analogue that is currently approved to treat breast, non-small cell lung, ovarian and pancreatic cancers and widely used to treat a variety of other cancers including bladder, biliary, colorectal and lymphoma.

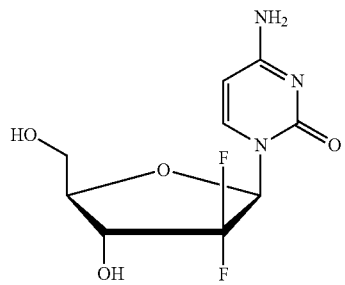

Gemcitabine's clinical utility is limited by a number of inherent and acquired resistance mechanisms. At the cellular level resistance is dependent on three parameters: (i) the down-regulation of deoxycytidine kinase, necessary for the activation into the phosphorylated moiety; (ii) the reduced expression of nucleoside transporters, in particular, hENT1 required for uptake by cancer cells; and (iii) the up-regulation of catalytic enzymes especially cytidine deaminase that degrades gemcitabine.

WO2005/012327 describes a series of nucleotide prodrugs for gemcitabine and related nucleoside drug molecules. Among them gemcitabine-[phenyl-benzoxy-L-alaninyl)]-phosphate (NUC-1031; 2) is identified as a particularly effective compound. These prodrugs appear to avoid many of the inherent and acquired resistance mechanisms which limit the utility of gemcitabine ('Application of ProTide Technology to Gemcitabine: A Successful Approach to Overcome the Key Cancer Resistance Mechanisms Leads to a New Agent (NUC-1031) in Clinical Development'; Slusarczyk et all; J. Med. Chem.; 2014, 57, 1531-1542).

NUC-1031 2 is typically prepared as a mixture of two diastereoisomers, epimeric at the phosphate centre (the S-epimer 3 and the R-epimer 4) which can be separated and administered as a single epimer.

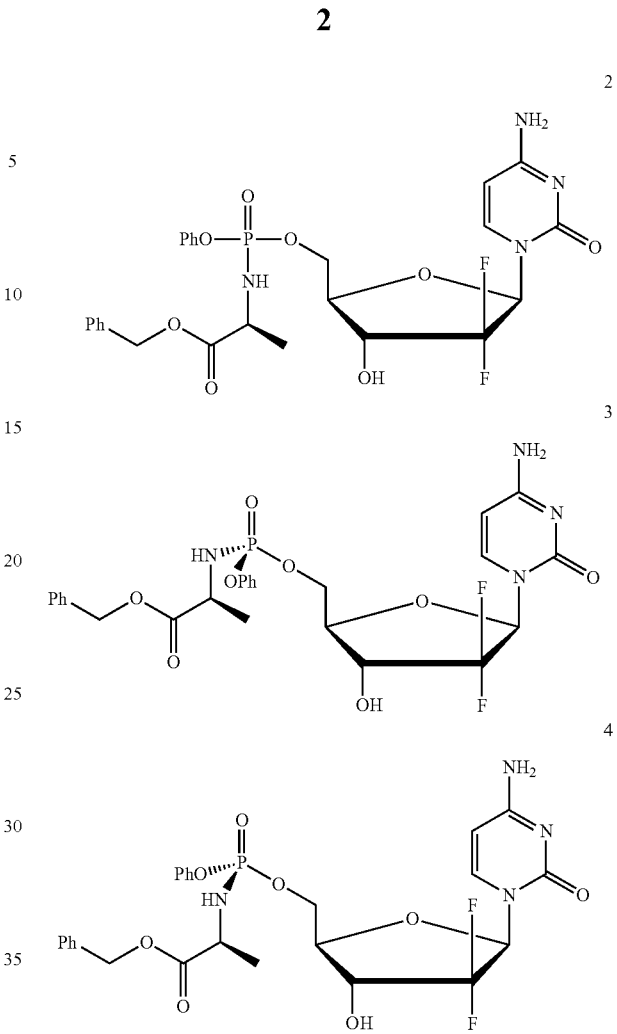

ProGem1 was a first-time-in-human (FTIH), phase I, open label, two stage study to investigate the safety, tolerability, clinical efficacy, pharmacokinetics (PK) and pharmacodynamics (PD) of NUC-1031 given in two parallel dosing schedules in subjects with advanced solid malignancies (EudraCT Number: 2011-005232-26). Subjects had the following tumour types at study entry: colorectal cancer (3 subjects), unknown primary (3), ovarian cancer (4), breast cancer (2), pancreatic cancer (3), cholangiocarcinoma (2), uterine or endometrial cancer (3), cervix cancer (1), lung cancer (2), mesothelioma (3) and thyroid cancer (1). The study confirmed NUC-1031's anti-tumour activity in patients with advanced progressive cancers, who have exhausted all standard therapeutic options, many of whom were resistant or refractory to prior nucleoside analogue therapy, including gemcitabine. Of particular note, the pharmacokinetic data showed that NUC-1031 as single agent generates around 10-fold higher $C_{max}$ intracellular levels of the active triphosphate moiety (dFdCTP) than single agent gemcitabine at equimolar dose. Moreover the analyses revealed that NUC-1031 releases less than half the levels of the toxic metabolite normally associated with gemcitabine.

Ovarian Cancer

Ovarian cancer is the sixth most commonly diagnosed cancer among women worldwide with an estimated 204,000 new cases diagnosed each year. The mortality rate is high with a 5 year survival rate of 45%, primarily because many women present with late stage disease but also because there is a high rate of disease recurrence and development of platinum-resistance. The initial therapy for advanced stage ovarian cancer is a combination of optimal surgical debulking and systemic treatment with a platinum plus taxane chemotherapy regimen. Even though complete response following treatment is observed in 70%, the majority will subsequently present with disease relapse within 2 years.

Therapy for recurrent disease is governed by the time between primary treatment and relapse. This is defined as the platinum-free interval (PFI): (1) Those with disease progression while receiving platinum-based therapy or within 4 weeks of last platinum dose are defined as having platinum-refractory disease; (2) those with a PFI of >1 month and less than 6 months have platinum-resistant disease; (3) those with a PFI of 6-12 months have partial platinum resistance; (4) and those with PFI>than 12 months have platinum-sensitive recurrence. According to NICE guidelines, those with platinum-resistant or refractory disease should then be treated with topotecan, liposomal doxorubicin, weekly paclitaxel or entered into a clinical study. Those with partially platinum-resistant recurrence should be treated with platinum-based regimens such as carboplatin with gemcitabine, carboplatin with liposomal doxorubicin or entered into a clinical study. Those with platinum-resistant disease should be retreated with carboplatin, either as monotherapy or in combination with paclitaxel. Unfortunately, those with platinum-resistant recurrence have a significantly shorter median overall survival (35 to 61 weeks) compared to those with platinum-sensitive disease (>104 weeks) suggesting that response to platinum is a key determinant for survival.

Chemotherapy Resistance in Ovarian Cancer

An almost inevitable result of repeated exposure to courses of platinum-based chemotherapy is the development of platinum resistance. This occurs via a number of mechanisms such as up-regulation of DNA damage repair and anti-apoptosis proteins, reduced copper transporters and increased drug efflux from the cancer cell. A rationale for combining platinum-based chemotherapy (such as carboplatin) with another chemotherapy agent, such as gemcitabine or liposomal doxorubicin, is to overcome resistance and improve sensitivity to platinum. Certainly, response to carboplatin alone in partially platinum resistant recurrence is inferior in comparison to when carboplatin is given in combination with gemcitabine or liposomal doxorubicin. Although the response to combination therapy is superior to platinum monotherapy, the overall prognosis for these patients is very poor and novel treatment strategies are needed for this population.

Gemcitabine in Ovarian Cancer

Gemcitabine in combination with platinum (e.g. carboplatin) is effective for relapsed ovarian cancer, even following previous platinum exposure, due to the ability of gemcitabine to reverse resistance associated with enhanced DNA repair. In the AGO-OVAR study 356 patients with platinum sensitive recurrent ovarian cancer were assigned to either carboplatin AUC5 alone or carboplatin AUC4 (day 1) plus gemcitabine 1000 mg/m$^2$ on days 1 & 8 every 3 weeks. After a median follow-up of 17 months, a median PFS of 8.6 months was observed (95% CI, 7.9 to 9.7 months) for gemcitabine plus carboplatin and 5.8 months (95% CI, 5.2 to 7.1 months) for carboplatin alone (HR 0.72 (95% CI, 0.58 to 0.90; P=0.0031)). A response rate of 47.2% (95% CI, 39.9% to 54.5%) was recorded for gemcitabine plus carboplatin and 30.9% (95% CI, 24.1% to 37.7%) for carboplatin alone (P=0.0016). In view of the improved response and survival, gemcitabine is usually given alongside carboplatin in the relapsed, platinum-sensitive setting.

The combination of carboplatin AUC4 (day 1) and gemcitabine 1000 mg/m$^2$ on (days 1 & 8) every 3 weeks was trialled in the control arm of the OCEANS study, a randomised study in patients with platinum-sensitive ovarian cancer. 242 patients received this combination and demonstrated an objective response rate of 57.4%, 48.3% partial response and a duration of response of 7.4 months. In women with platinum-resistant recurrence, gemcitabine given alongside carboplatin was shown in one study to have a global response rate of 47%. However, in view of the likely resistance to carboplatin and relatively poor cellular uptake of gemcitabine in these patients, other non-platinum regimens are generally favoured over carboplatin and gemcitabine.

It is an aim of this invention to provide a combination therapy for treating cancer. It is an aim of this invention to provide a therapy that is more effective than existing treatments.

Certain embodiments of this invention satisfy some or all of the above aims.

BRIEF SUMMARY OF THE DISCLOSURE

In accordance with the present invention there is provided gemcitabine-[phenyl-benzoxy-L-alaninyl)]-phosphate, or a pharmaceutically acceptable salt or solvate thereof for use in treating cancer in combination with platinum-based anticancer agent selected from carboplatin, dicycloplatin, oxaliplatin, satraplatin and nedaplatin The invention also provides gemcitabine-[phenyl-benzoxy-L-alaninyl)]-phosphate, or a pharmaceutically acceptable salt or solvate thereof in combination with a platinum-based anticancer agent selected from carboplatin, dicycloplatin, oxaliplatin, satraplatin and nedaplatin. The combination will typically be for use in treating cancer.

The invention also provides a platinum-based anticancer agent selected from carboplatin, dicycloplatin, oxaliplatin, satraplatin and nedaplatin for use in treating cancer in combination with gemcitabine-[phenyl-benzoxy-L-alaninyl)]-phosphate, or a pharmaceutically acceptable salt or solvate thereof.

The invention also provides a method of treating cancer, the method comprising administering to a subject in need thereof a therapeutically effective amount of gemcitabine-[phenyl-benzoxy-L-alaninyl)]-phosphate, or a pharmaceutically acceptable salt or solvate thereof, in combination with a platinum-based anticancer agent selected from carboplatin, dicycloplatin, oxaliplatin, satraplatin and nedaplatin.

The invention also provides gemcitabine-[phenyl-benzoxy-L-alaninyl)]-phosphate, or a pharmaceutically acceptable salt or solvate thereof, in combination with a platinum-based anticancer agent selected from carboplatin, dicycloplatin, oxaliplatin, satraplatin and nedaplatin for use in the manufacture of a medicament for treating cancer.

The invention also provides gemcitabine-[phenyl-benzoxy-L-alaninyl)]-phosphate, or a pharmaceutically acceptable salt or solvate thereof, for use in the manufacture of a medicament for treating cancer in combination with a platinum-based anticancer agent selected from carboplatin, dicycloplatin, oxaliplatin, satraplatin and nedaplatin.

The invention also provides a platinum-based anticancer agent selected from carboplatin, dicycloplatin, oxaliplatin, satraplatin and nedaplatin for use in the manufacture of a medicament for treating cancer in combination with gemcitabine-[phenyl-benzoxy-L-alaninyl)]-phosphate, or a pharmaceutically acceptable salt or solvate thereof.

The invention also provides a pharmaceutical formulation comprising gemcitabine-[phenyl-benzoxy-L-alaninyl)]-phosphate, or a pharmaceutically acceptable salt or solvate thereof, together with a platinum-based anticancer agent selected from carboplatin, dicycloplatin, oxaliplatin, satraplatin and nedaplatin, and at least one pharmaceutically acceptable excipient.

The formulation may contain a unit dosage of gemcitabine-[phenyl-benzoxy-L-alaninyl)]-phosphate and a unit dosage of the platinum-based anticancer agent. The unit dosages may be the same but will typically be different.

The invention also provides a two separate formulations to be used together, the formulations being:
- a first formulation comprising gemcitabine-[phenyl-benzoxy-L-alaninyl)]-phosphate, or a pharmaceutically acceptable salt or solvate thereof, and at least one pharmaceutically acceptable excipient; and
- a second formulation comprising a platinum-based anticancer agent selected from carboplatin, dicycloplatin, oxaliplatin, satraplatin and nedaplatin and at least one pharmaceutically acceptable excipient. The formulations may be in the form of a kit. The formulations (i.e. the kit comprising said formulations) will typically be for treating cancer.

The treatments of the present invention are based on the fact that the combination of the two agents (i.e. the gemcitabine-[phenyl-benzoxy-L-alaninyl)]-phosphate and the platinum-based anticancer agent) show greater efficiency when administered in combination than is the case when either is administered alone. The term 'in combination' or 'together' in the context of the present invention refers to the fact that the two agents are both administered to the same patient during the treatment period. The administration may be separate in the sense of being provided in separate doses or may be in the same dose. Administration may take place concurrently or in sequence either immediately one after the other or with a time interval in between the administration of the two agents. The term 'alone' in the context of this discussion thus means administration of only one active agent and no administration of the other agent during the treatment period, even after a time interval.

Combination therapy according to the invention embraces the co-administration or sequential administration of the two active agents in a manner which enhances the overall therapeutic result relative to the administration of one of the active agents alone during the overall treatment period. The pharmaceutical formulation(s) employed for the purpose may be individual, i.e. separate formulations, or presented in a single formulation. The or each formulation may be in a liquid form, either diluted or ready for dilution, or may be in a solid form. Solid forms may be provided for dissolution in a suitable solvent medium. Solid forms may also be presented in concentrated unit dosage form as tablets, capsules losanges etc.

In particular, the present inventors have found that plasma concentrations of the active metabolite of NUC-1031 dFdCTP (gemcitabine triphosphate) shortly after administration are considerably higher when NUC-1031 is administered to human patients in combination with carboplatin, an exemplary platinum-based anticancer agent, relative to when it is administered in the absence of carboplatin. The use of the two agents in combination thus provides an unexpected synergistic effect.

The positive clinical outcome and improved pharmacokinetic results achieved with NUC-1031 in combination with carboplatin are unexpected for two reasons: (i) single agent NUC-1031 achieved remarkably high levels of the active metabolite dFdCTP, which appeared to have reached enzymatic saturation, and (ii) the molecular mechanisms underpinning the synergistic effect observed for gemcitabine and platinums are not thought to be applicable to NUC-1031.

The enzyme nucleoside-diphosphate kinase (NDPK), converts dFdCDP into dFdCTP. NUC-1031 was thought to saturate the NDPK enzyme because in the clinic, as single agent, NUC-1031 generates 10-fold higher $C_{max}$ intracellular dFdCTP levels than single agent gemcitabine and 4-fold higher than gemcitabine in combination with carboplatin at equimolar dose. NUC-1031 overcomes all the key resistance mechanisms associated with gemcitabine to generate high levels of dFdCDP, which would saturate the NDPK enzyme. Gemcitabine, on the other hand, is a poor source of substrate for NDPK because of limited uptake by hENT1 (50% hENT1-deficient cancers) and extensive degradation by CDA (60% high CDA expression and activity in cancers) as well as poor activation by dCK (30% low dCK in cancers). Therefore, if these 3 resistance mechanisms are present in the tumour cells, for every 100 gemcitabine molecule administered only 9 may be converted into the NDPK substrate dFdCDP to generate dFdCTP. In contrast, because NUC-1031 metabolism is independent of these enzymes, out of 100 NUC-1031 molecules it might be expected that all 100 could become source of substrate for NDPK and saturate the enzyme.

(ii) The synergy observed for gemcitabine and platinums has been attributed to an increase by 1.5-fold in the active metabolite dFdCTP levels (van Moorsel et al., *British Journal of Cancer,* 1999, 80(7), 981-990), which has been described as the result of improved deoxycytidine kinase (dCK) activity. When combined with gemcitabine two platinum-based mechanisms have been suggested to increase dCK-mediated dFdCTP levels. The first cellular mechanism involves ribonucleotide reductase inhibition, the enzyme responsible for deoxycytidine triphosphate (dCTP) synthesis, known to inhibit dCK (Bajetta et al., *Annals of Oncology,* 2003, 14, 242-247). In the second molecular mechanism the platinum-induced DNA-damage activates the nucleotide excision repair processes, which require deoxyribonucleotides (dNTPs). In turn several enzymes implicated in dNTPs synthesis are up-regulated, including dCK (van Moorsel et al., 1999). NUC-1031 is synthesised as a nucleotide analogue, in the monophosphate form, which bypasses dCK-dependent dFdCTP formation and therefore the synergy observed combining NUC-1031 and carboplatin appears to originate from a different and yet unknown pathway.

In certain preferred embodiments, the platinum-based anticancer agent is carboplatin.

The gemcitabine-[phenyl-benzoxy-L-alaninyl)]-phosphate may be a mixture of phosphate diastereoisomers or it may be the (S)-epimer or as the (R)-epimer in substantially diastereomerically pure form. 'Substantially diastereomerically pure' is defined for the purposes of this invention as a diastereomeric purity of greater than about 90%. If present as a substantially diastereoisomerically pure form, the gemcitabine-[phenyl-benzoxy-L-alaninyl)]-phosphate may have a diastereoisomeric purity of greater than 95%, 98%, 99%, or even 99.5%.

The cancer may be a cancer selected from: pancreatic cancer, breast cancer, ovarian cancer, bladder cancer, colorectal cancer, lung cancer, billiary cancer, prostate cancer, cholangiocarcinoma, renal cancer, lymphoma, leukemia, cervical cancer, thymic cancer, a cancer of an unknown primary origin, oesophageal cancer, mesothelioma, adrenal cancer, cancer of the uterus, cancer of the fallopian tube, endometrial cancer, testicular cancer, head and neck cancer cancer of the central nervous system and germ cell tumours.

The cancer may be selected from lung cancer, bladder cancer, breast cancer and a gynaecological cancer. The cancer may be a gynaecological cancer (e.g. a cancer selected from cancer of the uterus, cancer of the fallopian tube, endometrial cancer, ovarian cancer and cervical cancer). Combinations in which the platinum-based anticancer agent is carboplatin are particularly preferred for treating these particular cancers. In certain preferred embodiments, the cancer is ovarian cancer. In certain particularly preferred embodiments, the cancer is ovarian cancer and the platinum-based anticancer agent is carboplatin The cancer (e.g. the ovarian cancer) may be relapsed. The cancer (e.g. the ovarian cancer) may be refractory, resistant or partially resistant to the platinum-based anticancer agent (e.g. carboplatin). The cancer (e.g. the ovarian cancer) may be sensitive to the platinum-based anticancer agent (e.g. carboplatin).

A solvate will typically be a hydrate. Thus, the gemcitabine-[phenyl-benzoxy-L-alaninyl)]-phosphate may be in the form of a salt or hydrate, or a solvate (e.g. hydrate of a salt). It may be that the gemcitabine-[phenyl-benzoxy-L-alaninyl)]-phosphate is not in the form of a salt and it may be that it is not in the form of a solvate or hydrate. Preferably, the gemcitabine-[phenyl-benzoxy-L-alaninyl)]-phosphate is in the form of the free base.

The gemcitabine-[phenyl-benzoxy-L-alaninyl)]-phosphate and the platinum-based anticancer agent may be administered simultaneously or they may be administered sequentially. Where they are administered simultaneously, they may be administered in a single formulation or they may be administered in separate formulations. Where they are administered sequentially, they may be administered on the same day or they may be administered on separate days during the treatment period. It may be that on certain days during the treatment period, the gemcitabine-[phenyl-benzoxy-L-alaninyl)]-phosphate and the platinum-based anticancer agent are administered simultaneously or on the same day and on certain other days in the treatment program a single one of the agents is administered.

NUC-1031 Formulations

The gemcitabine-[phenyl-benzoxy-L-alaninyl)]-phosphate may be administered parenterally, e.g. for intravenously, subcutaneously or intramuscularly. Preferably, the gemcitabine-[phenyl-benzoxy-L-alaninyl)]-phosphate is administered intravenously.

The gemcitabine-[phenyl-benzoxy-L-alaninyl)]-phosphate may be administered parenterally as an aqueous formulation which optionally also comprises a polar organic solvent, e.g. DMA. In the case of parenteral (e.g. intravenous) administration, the formulation preferably also comprises a polar aprotic organic solvent, e.g. DMA.

The formulation may be for dilution by a predetermined amount shortly before administration, i.e. up to 48 hours (e.g. up to 24, 12 or 2 hours) before administration.

The formulation may also comprise one or more pharmaceutically acceptable solubilizers, e.g. a pharmaceutically acceptable non-ionic solubilizers. Solubilizers may also be called surfactants or emulsifiers. Illustrative solubilizers include polyethoxylated fatty acids and fatty acid esters and mixtures thereof. Suitable solubilizers may be or comprose polyethoxylated castor oil (e.g. that sold under the trade name Kolliphor® ELP); or may be or comprise polyethoxylated hydroxy-stearic acid (e.g. that sold under the trade names Solutol® or Kolliphor® HS15); or may be or comprise polyethoxylated (e.g. polyoxyethylene (20)) sorbitan monooleate, (e.g. that sold under the trade name Tween® 80).

In certain preferred embodiments, the formulation comprises more than one pharmaceutically acceptable solubilizer.

The formulation may also comprise an aqueous vehicle. The formulation may be ready to administer, in which case it will typically comprise an aqueous vehicle.

The formulation may be for parenteral, e.g. for intravenous, subcutaneous or intramuscular administration. Preferably, the formulation is for intravenous administration. The administration may be through a central vein or it may be through a peripheral vein.

The total dose of gemcitabine-[phenyl-benzoxy-L-alaninyl)]-phosphate in a formulation suitable for administration will typically be from 250 mg to 3 g, e.g. from 1 g to 2 g, e.g. about 1.5 g.

It may be that the polar aprotic solvent (e.g. DMA) represents 30% or more by volume of the formulation. Thus, it may be that the polar aprotic solvent (e.g. DMA) represents 50% or more, e.g. 60% or more by volume of the formulation. The polar aprotic solvent (e.g. DMA) may represent 95% or less by volume of the formulation, e.g. 90% or less. The formulation may also comprise an aqueous vehicle (e.g. saline). The aqueous vehicle may be present in 50% or less by volume of the formulation, e.g. 30% or less by volume of the formulation. Typically the aqueous vehicle (e.g. saline) will represent 5% or more, e.g. 10% or more, by volume of the formulation.

It may be that the concentration of the gemcitabine-[phenyl-benzoxy-L-alaninyl)]-phosphate in the formulation solvent(s) is 500 mg or less per mL. It may be that the concentration 100 mg or more per mL. Preferably, the concentration is from 200 mg to 300 mg, e.g. from 225 mg to 275 mg, e.g. about 250 mg, per mL.

Certain preferred formulations comprise:
from 30% to 95% by volume DMA;
from 5% to 50% by volume aqueous vehicle; and
from 100 mg to 400 mg (e.g. from 100 mg to 300 mg) per mL gemcitabine-[phenyl-benzoxy-L-alaninyl)]-phosphate.

More preferred formulations comprise:
from 70% to 90% by volume DMA;
from 10% to 30% by volume aqueous vehicle (e.g. saline); and
from 200 mg to 300 mg per mL gemcitabine-[phenyl-benzoxy-L-alaninyl)]-phosphate.

The formulations described in the previous four paragraphs, in which the polar aprotic solvent (e.g. DMA) is present as a major component, may, for example, be used for administering gemcitabine-[phenyl-benzoxy-L-alaninyl)]-phosphate in the form of a mixture of phosphate diastereoisomers. They can also be used to administer gemcitabine-[phenyl-benzoxy-L-alaninyl)]-phosphate in the form of the (S)-phosphate epimer in substantially diastereomerically pure form. The formulations described in these paragraphs can be used by administering (e.g. by infusion or injection) the formulation without it being diluted prior to administration. They may be administered through a central vein.

Alternatively, these formulations may be diluted to form a formulation suitable for administration through a peripheral vein.

It may be that the polar aprotic solvent (e.g. DMA) represents 10% or more, e.g. 20% or more by volume of the formulation. Thus, it may be that the polar aprotic solvent (e.g. DMA) represents 80% or less, e.g. 60% or less by volume of the formulation. The polar aprotic solvent (e.g. DMA) may represent 40% or less by volume of the formulation. The formulation may also comprise one or more solubilizers (e.g. one or more polyethoxylated fatty acids). The one or more solubilizers may represent 90% or less by volume of the formulation, e.g. 80% or less by volume of the formulation. Typically the one or more solubilizers will represent 30% or more, e.g. 50% or more or 60% or more, by volume of the formulation. One preferred formulation comprises the drug as a solution in a 30%:70% DMA: solubilizer mixture.

It may be that the concentration of the gemcitabine-[phenyl-benzoxy-L-alaninyl)]-phosphate in the formulation solvent(s) is 200 mg or less per mL, e.g. 150 mg or less or 120 mg or less. It may be that the concentration is 40 mg or more per mL, e.g. 60 mg or more. Preferably, the concentration is from 70 mg to 110 mg, e.g. about 75 mg or about 100 mg, per mL.

Certain preferred formulations comprise:
from 20% to 80% by volume DMA;
from 30% to 80% by volume solubilizer or solubilizers; and
from 50 mg to 150 mg per mL gemcitabine-[phenyl-benzoxy-L-alaninyl)]-phosphate. The formulation may also comprise an aqueous vehicle, e.g. in an amount from 1% to 15% by volume.

Certain particularly preferred formulations comprise:
from 20% to 80% by volume DMA;
from 20% to 60% by volume a first solubilizer;
from 5% to 40% by volume a second solubilizer;
from 2% to 12% an aqueous vehicle; and
from 50 mg to 150 mg per mL gemcitabine-[phenyl-benzoxy-L-alaninyl)]-phosphate. The first solubilizer may be a polyethoxylated castor oil (e.g. that sold under the trade name Kolliphor® ELP). The second solubilizer may be a polyethoxylated sorbitan monooleate (e.g. that sold under the trade name Tween® 80). The formulation may also comprise an aqueous vehicle, e.g. in an amount from 3% to 15% by volume.

The formulation may comprise:
from 50% to 60% by volume DMA;
from 20% to 30% by volume the first solubilizer;
from 8% to 15% by volume the second solubilizer;
from 4% to 10% an aqueous vehicle; and
from 75 mg to 125 mg per mL gemcitabine-[phenyl-benzoxy-L-alaninyl)]-phosphate.

The formulations described in the previous five paragraphs, in which the polar aprotic solvent (e.g. DMA) is present as a major component, can be used, for example, for administering gemcitabine-[phenyl-benzoxy-L-alaninyl)]-phosphate in the form of the (S)-phosphate epimer in substantially diastereomerically pure form. They can also be used for administering a mixture of R and S epimers or the R epimer. The formulations described in these paragraphs are typically diluted with an aqueous vehicle prior to administration. Once diluted, they may be administered through a peripheral vein.

These formulations may be formed by diluting a formulation that does not contain any solubilizers. Gemcitabine-[phenyl-benzoxy-L-alaninyl)]-phosphate can degrade in the presence of certain solubilizers.

It may be that the polar aprotic solvent (e.g. DMA) represents 0.1% or more, e.g. 0.5% or more or 1% or more by volume of the formulation. Thus, it may be that DMA represents 10% or less, e.g. 5% or less or 3% or less by volume of the formulation. The polar aprotic solvent (e.g. DMA) may represent 8% or less or 2% or less by volume of the formulation. The formulation may also comprise an aqueous vehicle (e.g. WFI). The aqueous vehicle may be present in 99.5% or less by volume of the formulation, e.g. 99% or 98% or less by volume of the formulation. Typically the aqueous vehicle will represent 85% or more, e.g. 90% or more or 95% or more, by volume of the formulation. The formulation may also comprise one or more solubilizers (e.g. one or more polyethoxylated fatty acids). The one or more solubilizers may represent in 10% or less by volume of the formulation, e.g. 7.5% or less or 5% or less or 3% or less by volume of the formulation. Typically the one or more solubilizers will represent 0.1% or more, e.g. 0.5% or more or 1% or more or 2% or more, by volume of the formulation.

It may be that the concentration of the gemcitabine-[phenyl-benzoxy-L-alaninyl)]-phosphate in the formulation solvent(s) is 12.0 mg or less per mL or 10.0 mg or less per mL, e.g. 7.0 mg or less or 4.5 mg or less per mL. It may be that the concentration is 1.0 mg or more per mL, e.g. 2.0 mg or more. Preferably, the concentration is from 2.5 mg to 11 mg per mL, e.g. from 3 mg to 7 mg per mL, e.g. about 4.5 mg per mL.

Certain preferred formulations comprise:
from 0.1% to 15% (e.g. 0.5 to 5%) by volume DMA;
from 0.1% to 15% (e.g. 0.1% to 7.5%) by volume solubilizer or solubilizers;
from 85% to 99% by volume aqueous vehicle; and
from 2.0 mg to 12.0 mg (e.g. from 2.0 mg to 10.0 mg) per mL gemcitabine-[phenyl-benzoxy-L-alaninyl)]-phosphate.

Certain particularly preferred formulations comprise:
from 0.5% to 10% by volume DMA;
from 0.2% to 4% by volume a first solubilizer;
from 0.1% to 2% by volume a second solubilizer;
from 85% to 99% by volume aqueous vehicle; and
from 2.0 mg to 12.0 mg (e.g. from 2.0 mg to 10.0 mg) per mL gemcitabine-[phenyl-benzoxy-L-alaninyl)]-phosphate. The first solubilizer may be a polyethoxylated castor oil (e.g. that sold under the trade name Kolliphor® ELP). The second solubilizer may be a polyethoxylated sorbitan monooleate (e.g. that sold under the trade name Tween® 80).

The formulation may comprise:
from 0.5% to 6% by volume DMA;
from 0.5% to 6% by volume a first solubilizer;
from 0.2% to 4% by volume a second solubilizer;
from 85% to 99% by volume aqueous vehicle; and
from 2.0 mg to 12.0 mg (e.g. from 2.0 mg to 10.0 mg) per mL gemcitabine-[phenyl-benzoxy-L-alaninyl)]-phosphate.

The formulations described in the previous four paragraphs, in which the polar aprotic solvent (e.g. DMA) is present as a minor component, can be used, for example, for administering gemcitabine-[phenyl-benzoxy-L-alaninyl)]-phosphate in the form of the (S)-phosphate epimer in substantially diastereomerically pure form. They can also be used for administering a mixture of R and S epimers or the R epimer. The formulations described in these paragraphs will typically have been prepared by diluting a concentrated polar aprotic solvent (e.g. DMA) formulation or concentrated polar aprotic solvent (e.g. DMA) and solubilizer formulation with the aqueous vehicle up to 48 hours prior to administration. The resulting formulations may be administered through a peripheral vein.

While gemcitabine-[phenyl-benzoxy-L-alaninyl)]-phosphate is preferably formulated for parenteral administration, in certain embodiments of the invention it may be administered orally.

Any of the above mentioned formulations may also comprise the platinum-based anticancer agent.

Kits

The invention provides a kit for treating cancer, the kit comprising:
- a first formulation comprising gemcitabine-[phenyl-benzoxy-L-alaninyl)]-phosphate, or a pharmaceutically acceptable salt or solvate thereof, and at least one pharmaceutically acceptable excipient; and
- a second formulation comprising a platinum-based anticancer agent and at least one pharmaceutically acceptable excipient.

In certain particular embodiments, the kit may comprise:
- a first formulation comprising:
   - from 30% to 95% by volume DMA;
   - from 5% to 50% by volume aqueous vehicle; and
   - from 100 mg to 400 mg (e.g. from 100 mg to 300 mg) per mL gemcitabine-[phenyl-benzoxy-L-alaninyl)]-phosphate;
- a second formulation comprising a platinum-based anticancer agent and at least one pharmaceutically acceptable excipient; and
- a third formulation comprising:
   - from 30% to 95% by volume DMA;
   - from 5% to 50% by volume aqueous vehicle.

The third formulation will typically not comprise an active. Thus, it will typically comprise neither gemcitabine-[phenyl-benzoxy-L-alaninyl)]-phosphate nor a platinum-based anticancer agent. The third formulation may be provided in two separate vessels or in a single vessel.

The kit mentioned in the previous two paragraphs is useful where the gemcitabine-[phenyl-benzoxy-L-alaninyl)]-phosphate is administered intravenously via a central line. The central line is flushed with the third formulation prior to administration of the first formulation. This mitigates the risk of precipitation of gemcitabine-[phenyl-benzoxy-L-alaninyl)]-phosphate in or at the entrance to the intravenous administration apparatus, i.e. the central line, by avoiding the direct contact of the active formulation with aqueous media (e.g. a saline flushing solution). The central line may also be flushed with the third formulation after administration of the first formulation. This further prevents precipitation.

In certain particular embodiments, the kit may comprise:
- a first formulation comprising:
   - from 30% to 95% by volume DMA;
   - from 5% to 50% by volume aqueous vehicle; and from 100 mg to 400 mg (e.g. from 100 mg to 300 mg) per mL gemcitabine-[phenyl-benzoxy-L-alaninyl)]-phosphate;
- a second formulation comprising a platinum-based anticancer agent and at least one pharmaceutically acceptable excipient; and
- a third formulation comprising:
   - from 20% to 80% by volume DMA;
   - from 20% to 60% by volume a first solubilizer;
   - from 10% to 40% by volume a second solubilizer.

Typically the third formulation will not comprise any active. Thus, it will typically comprise neither gemcitabine-[phenyl-benzoxy-L-alaninyl)]-phosphate nor a platinum-based anticancer agent.

The kit mentioned in the previous two paragraphs is useful where the gemcitabine-[phenyl-benzoxy-L-alaninyl)]-phosphate is administered intravenously via a peripheral vein. The first formulation is diluted with the third formulation up to 48 h, e.g. up to 24 h before administration to form a fourth formulation. The fourth formulation is further diluted with an aqueous vehicle before administration to the desired concentration to form the formulation which is used administered by infusion or injection to the patient. In order to achieve formulations for peripheral administration which are stable with respect to precipitation of gemcitabine-[phenyl-benzoxy-L-alaninyl)]-phosphate, it is typically desirable to include solubilizers. However, the gemcitabine-[phenyl-benzoxy-L-alaninyl)]-phosphate can be prone to degradation in the presence of such solubilizers. Thus, a two stage dilution method is, in certain embodiments of the invention, the preferable means by which formulations of gemcitabine-[phenyl-benzoxy-L-alaninyl)]-phosphate for peripheral administration are achieved.

Formulations of the Platinum-Based Anticancer Agent

The platinum-based anticancer agent may be administered parenterally, e.g. intravenously, intraperitoneally, subcutaneously or intramuscularly. Preferably, the platinum-based anticancer agent is administered intravenously.

The platinum-based anticancer agent will typically be administered as an aqueous solution, e.g. as a sterile, pyrogen-free, 10 mg/mL aqueous solution. Further information on the administration of carboplatin is available, for example, on the US FDA approved label for Paraplatin®.

Carboplatin is typically administered by infusion into a vein but it may be administered intraperitoneally. Where carboplatin is administered intravenously, this may be done over 15 to 60 minutes or it may be over a longer period, e.g. continuous IV infusion over 24 hours.

Dosage Regimens

It may be that the NUC-1031 is administered twice in a 21 day cycle. It may be that the platinum-based anticancer agent (e.g. carboplatin) is administered once in the 21 day cycle. In a preferred dosage regimen NUC-1031 is administered on day 1 and day 8 of a 21 day cycle and the platinum-based anticancer agent (e.g. carboplatin) is administered on day 1 of the 21 day cycle. It may be that NUC-1031 and the platinum-based anticancer agent (e.g. carboplatin) are administered simultaneously on day 1 of a 21 day cycle.

The dose of NUC-1031 administered at each administration event is preferably between 250 mg/m$^2$ and 1250 mg/m$^2$. The dose of NUC-1031 administered at each administration event may be between 300 mg/m$^2$ and 1000 mg/m$^2$. The dose of NUC-1031 administered at each administration event may be between 400 mg/m$^2$ and 800 mg/m$^2$. The dose of NUC-1031 administered at each administration event may be about 500 mg/m$^2$ or about 750 mg/m$^2$.

The dose of the platinum-based anticancer agent (e.g. carboplatin) administered at each administration event may be selected to provide an AUC of between 2 and 5.5 mgmL$^{-1}$ min$^{-1}$. It may be selected to provide an AUC of between 2.5 and 4.5 mgmL$^{-1}$ min$^{-1}$. It may be sufficient to provide an AUC of about 3 or about 4 mgmL$^{-1}$ min$^{-1}$.

It may be that the dose of NUC-1031, or the dose of the platinum-based anticancer agent (e.g. carboplatin), or the dose of both of the compounds, remains substantially the same in each treatment cycle. For example, a dose of NUC-1031 of about 750 mg/m$^2$ per administration event, and a dose of carboplatin selected to provide an AUC of about 4 mgmL$^{-1}$ min$^{-1}$ may be used in multiple treatment cycles. Similarly, a dose of NUC-1031 of about 500 mg/m$^2$ per administration event, and a dose of carboplatin selected to provide an AUC of about 4 mgmL$^{-1}$ min$^{-1}$ may be used in multiple treatment cycles.

Alternatively, it may be that the dose of NUC-1031, or the dose of the platinum-based anticancer agent (e.g. carboplatin), or the dose of both of the compounds, decreases from the first treatment cycle to the second (or subsequent) treatment cycle. For example, the dose of NUC-1031 administered at each administration event may decrease from about 750 mg/m$^2$, in a first treatment cycle, to about 500 mg/m$^2$ in a second (or subsequent) treatment cycle. The dose of the platinum-based anticancer agent (e.g. carboplatin) may decrease from one selected to provide an AUC of about 5 mgmL$^{-1}$ min$^{-1}$ in a first cycle of treatment, to one selected to provide an AUC of about 4 mgmL$^{-1}$ min$^{-1}$, or an AUC of about 3 mgmL$^{-1}$ min$^{-1}$ in a second (or subsequent) treatment cycle.

Suitable treatment regimens may make use of decreases (as set out in the preceding paragraph) in both doses of NUC-1031 and doses of the platinum-based anticancer agent (e.g. carboplatin) from a first treatment cycle to a second (or subsequent) treatment cycle. For example, the dose of NUC-1031 administered at each administration event may decrease from about 750 mg/m$^2$, in a first treatment cycle, to about 500 mg/m$^2$ in a second (or subsequent) treatment cycle, and the dose of the platinum-based anticancer agent (e.g. carboplatin) may decrease from one selected to provide an AUC of about 5 mgmL$^{-1}$ min$^{-1}$ in a first cycle of treatment, to one selected to provide an AUC of about 4 mgmL$^{-1}$ min$^{-1}$, or one selected to provide an AUC of about 3 mgmL$^{-1}$ min$^{-1}$ in a second (or subsequent) treatment cycle.

In the event that the dose of NUC-1031 decreases from a first to a second, or subsequent, treatment cycle (such as from about 750 mg/m$^2$ per administration incident, to about 500 mg/m$^2$ per administration incident), the dose of the platinum-based anticancer agent (e.g. carboplatin) may remain the same between the first and second, or subsequent, treatment cycles (for example, a dose selected to provide an AUC of about 4 mgmL$^{-1}$ min$^{-1}$ in each cycle).

In the event that the dose of NUC-1031 remains constant from a first to a second, or subsequent, treatment cycle (such as about 500 mg/m$^2$ per administration incident), the dose of the platinum-based anticancer agent (e.g. carboplatin) may decrease between the first and second, or subsequent, treatment cycles (for example, from a dose selected to provide an AUC of about 5 mgmL$^{-1}$ min$^{-1}$ in a first treatment cycle to for example, to a dose selected to provide an AUC of about 4 mgmL$^{-1}$ min$^{-1}$ in a second, or subsequent, treatment cycle).

The inventors have found that the above mentioned dosage regimen provide a balance in which the toxicity of each of the components of the combination is at an acceptable level yet a therapeutic benefit from the combination is still observed.

It may be that the above mentioned dosage regimen provides an improved survival rate in patients. It may be that it provides a stable disease in greater than 50% of patients. It may be that it provides a reduction of CA125 of greater than 50% in greater than 50% of patients. It may be that it provides one or more of the above benefits with an acceptable level of side-effects. It may be that the dosage is such that the AUC of dFdCTP is higher for the combination than for NUC-1031 administered as a single agent. It may be that the dosage is such that the ration of AUC to $C_{max}$ of dFdCTP is higher for the combination than for NUC-1031 administered as a single agent.

BRIEF DESCRIPTION OF THE DRAWINGS

Embodiments of the invention are further described hereinafter with reference to the accompanying drawings, in which.

DETAILED DESCRIPTION

Figure 1:
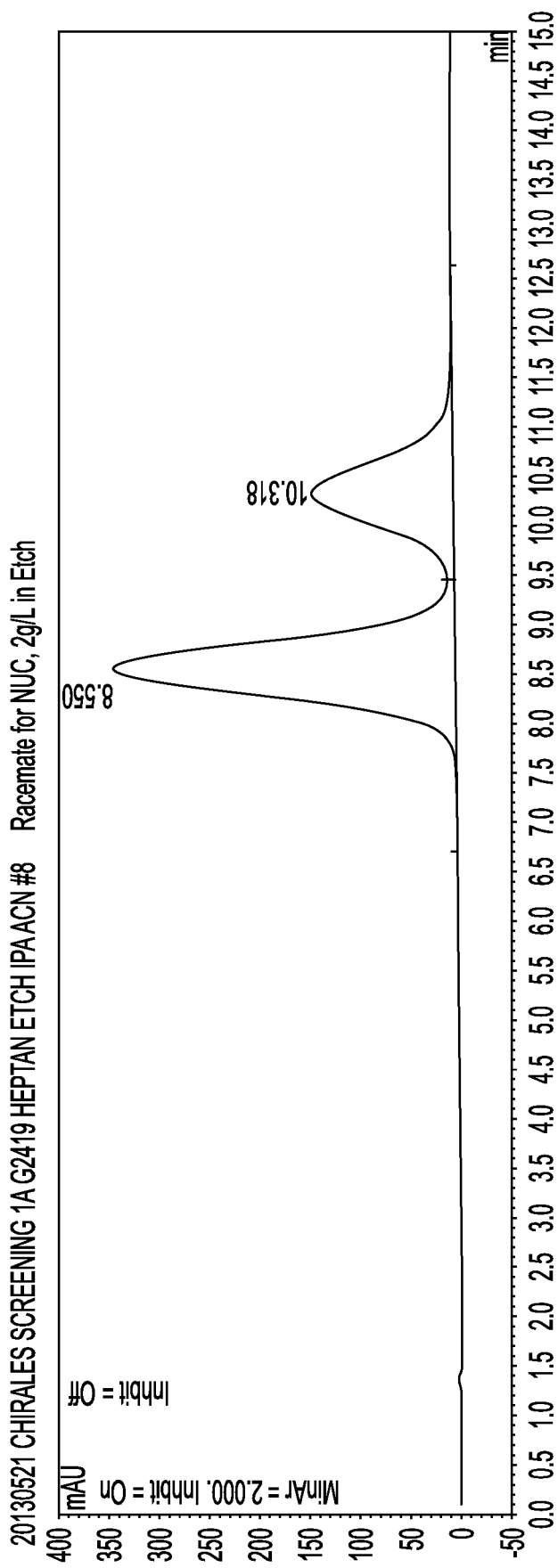
FIG. 1 shows the chromatograph for separation of compounds 3 and 4 by HPLC using a Chiralpak AD column and a n-heptane/IPA gradient solvent system

'Simultaneous' is intended to mean "substantially simultaneous" e.g. less than 30 mins apart. 'Sequential' means administration more than 30 mins apart.

Throughout this specification, the term S-epimer or S-diastereoisomer refers to gemcitabine-[phenyl-benzoxy-L-alaninyl)]-(S)-phosphate. Likewise, throughout this specification, the term R-epimer or R-diastereoisomer refers to gemcitabine-[phenyl-benzoxy-L-alaninyl)]-(R)-phosphate.

The compounds of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate, hemioxalate and hemicalcium salts. In certain embodiments, particularly those that apply to the s-epimer, the compound is in the form of a HCl salt or a hemioxalate salt.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered parenterally, then the dosage of the compound of the invention may be in the range from 0.1 to 5 g/m$^2$, e.g. from 0.5 to 2 g/m$^2$. The size of the dose for therapeutic purposes of compounds of the invention will naturally vary according to the nature and severity of the conditions, the age and sex of the animal or patient and the route of administration, according to well known principles of medicine.

Dosage levels, dose frequency, and treatment durations of compounds of the invention are expected to differ depending on the formulation and clinical indication, age, and co-morbid medical conditions of the patient.

The appropriate dose to obtain a desired AUC of carboplatin may be calculated using the Calvert formula.

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For parenteral (e.g. intravenous) administration the compounds may be administered as a sterile aqueous or oily solution. The compounds of the invention are very lipophillic. Aqueous formulations will typically, therefore, also contain a pharmaceutically acceptable polar organic solvent.

The size of the dose for therapeutic purposes of compounds of the invention will naturally vary according to the nature and severity of the conditions, the age and sex of the animal or patient and the route of administration, according to well known principles of medicine.

Dosage levels, dose frequency, and treatment durations of compounds of the invention are expected to differ depending on the formulation and clinical indication, age, and co-morbid medical conditions of the patient.

The present invention also includes all pharmaceutically acceptable isotopically-labelled forms of compounds 2, 3 or 4 wherein one or more atoms are replaced by atoms having the same atomic number, but an atomic mass or mass number different from the atomic mass or mass number of the predominant isotope usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

The method of treatment or the compound for use in the treatment of cancer may involve, in addition to the gemcitabine-[phenyl-benzoxy-L-alaninyl)]-phosphate and the platinum-base anticancer compound, conventional surgery or radiotherapy or chemotherapy. Such chemotherapy may include the administration of one or more other active agents.

Thus, the, each or any one of the pharmaceutical formulations may comprise another active agent.

The one or more other active agents may be one or more of the following categories of anti-tumour agents:
(i) antiproliferative/antineoplastic drugs and combinations thereof, such as alkylating agents (for example cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 50-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, clopredenol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine; or compounds that inhibit PD-1, PD-L1 and CAR T.

The one or more other active agents may also be antibiotics.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Example 1—Single Diastereoisomers of NUC-1031

The (R) and (S) isomers can be separated by HPLC under the following conditions:
Equipment: Agilent 1200™ series with DAD detector
Flow rate: 1.0 mL/min
Column: Chiralpak AD™; 250×4.6 mm ID (normal phase)
Temperature: ambient
Particle size: 20 μm
Feed: dissolved in MeOH; 10 g/L
Solvent: n-heptane/IPA 10->50% isopropyl alcohol
The chromatogram is shown in FIG. 1. The (S)-epimer eluted at 8.6 min and the (R)-epimer eluted at 10.3 minutes.

Characterisation Methods and Materials:
Proton ($^1$H), carbon ($^{13}$C), phosphorus ($^{31}$P) and fluorine ($^{19}$F) NMR spectra were recorded on a Bruker Avance 500 spectrometer at 25° C. Spectra were auto-calibrated to the deuterated solvent peak and all $^{13}$C NMR and $^{31}$P NMR were proton-decoupled. The purity of final compounds was verified to be >95% by HPLC analysis using Varian Polaris C18-A (10 μM) as an analytic column with a gradient elution of H$_2$O/MeOH from 100/0 to 0/100 in 35 min. The HPLC analysis was conducted by Varian Prostar (LC Workstation-Varian prostar 335 LC detector).

2'-Deoxy-2',2'-difluoro-D-cytidine-5'-O-[phenyl(benzyloxy-L-alaninyl)]-(S)-phosphate 3

(ES+) m/z, found: (M+Na$^+$) 603.14. C$_{25}$H$_{27}$F$_2$N$_4$O$_8$NaP required: (M$^+$) 580.47.
$^{31}$P NMR (202 MHz, MeOD): $\delta_P$ 3.66
$^1$H NMR (500 MHz, MeOD): $\delta_H$ 7.58 (d, J=7.5 Hz, 1H, H-6), 7.38-7.32 (m, 7H, ArH), 7.26-7.20 (m, 3H, ArH), 6.24 (t, J=7.5 Hz, 1H, H-1'), 5.84 (d, J=7.5 Hz, 1H, H-5), 5.20 (AB system, J$_{AB}$=12.0 Hz, 2H, OCH$_2$Ph), 4.46-4.43 (m, 1H, H-5'), 4.36-4.31 (m, 1H, H-5'), 4.25-4.19 (m, 1H, H-3'), 4.07-4.00 (m, 2H, H-4', CHCH$_3$), 1.38 (d, J=7.2 Hz, 3H, CHCH$_3$).
$^{19}$F NMR (470 MHz, MeOD): $\delta_F$ −118.0 (d, J=241 Hz, F), −120.24 (broad d, J=241 Hz, F).
$^{13}$C NMR (125 MHz, MeOD): $\delta_C$ 174.61 (d, $^3J_{C-P}$=5.0 Hz, C=O, ester), 167.63 (C—NH$_2$), 157.74 (C=O base), 152.10 (d, $^2J_{C-P}$=7.0 Hz, C—Ar), 142.40 (CH-base), 137.22 (C—Ar), 130.90, 129.63, 129.39, 129.32, 126.32 (CH—Ar), 124.51 (d, $^1J_{C-F}$=257 Hz, CF$_2$), 121.47, 121.43 (CH—Ar), 96.67 (CH-base), 85.92 (broad signal, C-1'), 80.31 (C-4'), 71.27 (apparent t, $^2J_{C-F}$=23.7 Hz, C-3'), 68.03 (OCH$_2$Ph), 65.73 (d, $^2J_{C-P}$=5.30 Hz, C-5'), 51.66 (CHCH$_3$), 20.42 (d, $^3J_{C-P}$=6.25 Hz, CHCH$_3$).
Reverse HPLC, eluting with H$_2$O/MeOH from 100/0 to 0/100 in 35 min, showed one peak of diastereoisomer with $t_R$=22.53 min.

2'-deoxy-2',2'-difluoro-D-cytidine-5'-O-[phenyl(benzyloxy-L-alaninyl)]-(R)-phosphate 4

(ES+) m/z, found: (M+Na$^+$) 603.14. C$_{25}$H$_{27}$F$_2$N$_4$O$_8$NaP required: (M') 580.47.
$^{31}$P NMR (202 MHz, MeOD): $\delta_P$ 3.83
$^1$H NMR (500 MHz, MeOD): $\delta_H$ 7.56 (d, J=7.5 Hz, 1H, H-6), 7.38-7.31 (m, 7H, ArH), 7.23-7.19 (m, 3H, ArH), 6.26 (t, J=7.5 Hz, 1H, H-1'), 5.88 (d, J=7.5 Hz, 1H, H-5), 5.20 (s, 2H, OCH$_2$Ph), 4.49-4.46 (m, 1H, H-5'), 4.38-4.34 (m, 1H, H-5'), 4.23-4.17 (m, 1H, H-3'), 4.07-4.01 (m, 2H, H-4', CHCH$_3$), 1.38 (d, J=7.2 Hz, 3H, CHCH$_3$).
$^{19}$F NMR (470 MHz, MeOD): $\delta_F$ −118.3 (d, J=241 Hz, F), −120.38 (broad d, J=241 Hz, F).
$^{13}$C NMR (125 MHz, MeOD): $\delta_C$ 174.65 (d, $^3J_{C-P}$=5.0 Hz, C=O, ester), 167.65 (C—NH$_2$), 157.75 (C=O base), 152.10 (d, $^2J_{C-P}$=7.0 Hz, C—Ar), 142.28 (CH-base), 137.50 (C—Ar), 130.86, 129.63, 129.40, 129.32, 126.31 (CH—Ar), 124.50 (d, $^1J_{C-F}$=257 Hz, CF$_2$), 121.44, 121.40 (CH—Ar), 96.67 (CH-base), 85.90 (broad signal, C-1'), 80.27 (C-4'), 71.30 (apparent t, $^2J_{C-F}$=23.7 Hz, C-3'), 68.02 (OCH$_2$Ph), 65.50 (C-5'), 51.83 (CHCH$_3$), 20.22 (d, $^3J_{C-P}$=7.5 Hz, CHCH$_3$).
Reverse HPLC, eluting with H$_2$O/MeOH from 100/0 to 0/100 in 35 min, showed one peak of diastereoisomer with $t_R$=21.87 min.

Example 2—Clinical Study of Combination of NUC-1031 and Carboplatin in Patients with Recurrent Ovarian Cancer A Phase IB open label, dose-escalation study, PRO-002, was conducted to assess the safety, pharmacokinetics and clinical activity of NUC-1031 given on days 1 & 8 with carboplatin on day 1, q3-weekly for 6 cycles in participants with recurrent ovarian cancer.

TABLE 1

Demographic summary of the patients treated in the study

| | |
|---|---|
| Patients | 10 |
| Evaluable Patients (completed 3 cycles) | 10 |
| Age (mean) | 62 (range 37-77) |
| Prior Chemo Regimens (mean) | 3.1 (range 2-6) |

TABLE 2 summary of treatment efficacy

| | |
|---|---|
| Complete Response | 10% (n = 1) |
| Partial Response | 10% (n = 1) |
| Stable Disease | 80% (n = 8) |
| Disease Control Rate | 100% (n = 10) |
| Progression free survival (PFS) | 5.4+ months |

TABLE 3

Summary of patient responses

| Pt | Age | Primary Diagnosis | Prior Chemo | Prior Gem | PFI Months | NUC-1031 Cycles | Best RECIST Response | CA 125 Baseline | Lowest | Reduction | GCIG | PFS Months |
|---|---|---|---|---|---|---|---|---|---|---|---|---|
| 001 | 54 | Grade 3, Stage 3b | 2 | N | 7 | 6 | Partial Response All target lesions gone | 218 | 27 | 88% | PR | 9+ |

TABLE 3-continued

Summary of patient responses

| Pt | Age | Primary Diagnosis | Prior Chemo | Prior Gem | PFI Months | NUC-1031 Cycles | Best RECIST Response | CA 125 Baseline | CA 125 Lowest | CA 125 Reduction | GCIG | PFS Months |
|---|---|---|---|---|---|---|---|---|---|---|---|---|
| 002 | 68 | Grade 3, Stage 4 | 5 | Y | 0 | 6 | Stable Disease 14% Reduction | 865 | 377 | 56% | PR | 7+ |
| 003 | 37 | Grade 3, Stage 3b | 6 | Y | 0 | 6 | Stable Disease 5% Reduction | 272 | 117 | 57% | PR | 5 |
| 004 | 63 | Grade 3, Stage 4 | 3 | N | 8 | 4.5 | Stable Disease 22% Reduction | 1,574 | 447 | 72% | PR | 3 |
| 005 | 75 | Grade 3, Stage 4 | 3 | N | 3 | 6 | Stable Disease 26% Reduction | 638 | 127 | 80% | PR | 5+ |
| 006 | 70 | Grade 3, Stage 3c | 3 | Y | 0 | 6 | Stable Disease 28% Reduction | 48 | 25 | 48% | SD | 6+ |
| 007 | 77 | Large Cell Endocrine | 2 | N | 14 | 6 | Complete Response | | | | | 5+ |
| 008 | 54 | Grade 3, Stage 3c | 2 | Y | 7 | 6 | Stable Disease 28% Reduction | 791 | 23 | 97% | PR | 5+ |
| 009 | 63 | Grade 3, Stage 4 | 2 | Y | 4 | 6 | Stable Disease 2% Reduction | 75 | 42 | 44% | SD | 5+ |
| 010 | 76 | Grade 3, Stage 3c | 2 | Y | 5 | 6 | Stable Disease | 304 | 353 | — | SD | 4+ |

Pt = patient;
Chemo = chemotherapy;
Gem = gemcitabine;
PFI = Platinum Free Interval;
GCIG = Gynaecological Cancer InterGroup;
PR = Partial Response;
SD = Stable Disease;
PFS = Progression Free Survival;
+Ongoing at time of data cut-off.

The detail of each patient and their treatment regime is reproduced below:

The patients received NUC-1031 (Acelarin) was administered as a slow bolus intravenous injection on days 1& 8 of a 21 day-cycle regimen alongside carboplatin on day 1 of a 21 day regimen. Each patient received up to 6 cycles of treatment.

NUC-1031 is presented as a single dose intravenous injection in a clear vial containing 250 mg/ml NUC-1031 in a solution of dimethylacetamide (DMA) and normal saline in the ratio of 80:20. The product is a clear yellow solution, free from visible particles In the study most patients were treated with the S-epimer of Acelerin. Several patients received a 2:1 mixture of the S:R epimers. There is not believed to be any significant pharmacological difference between the two epimers but it has been found that the S-epimer is easier to formulate.

Patient 001

Diagnosis: Recurrent, partially platinum sensitive stage IIIb grade 3 serous carcinoma of the ovary. BRCA negative. Platinum Free Interval (PFI) 7 months.

Age 54 years, PS=0

Diagnosed in 2012. May 2012 had primary debulking surgery to total macroscopic clearance.

1. Completed 6 Cycles carboplatin+paclitaxel chemotherapy (ICON 8) in October 2012.

2. July 2013-January 2014, Received 6 Cycles of carboplatin+caelyx on chemotherapy arm of DESKTOP Study. September 2014: Progressive disease with increased peritoneal nodularity and new lung metastases.

Commenced on study 27 Nov. 2014. NUC-1031 750 mg/m$^2$ and carboplatin AUC4, and has completed the study (6 Cycles). Patient remains very well.

Efficacy: PET scan on 12 Dec. 2014 showed significant response to study drug with decrease in size and metabolic activity at target lesions. Significant reduction in CA125, now at normal levels from a baseline of 218. CT scan on 21 Jan. 2015 showed Partial Response RECIST. Two target lesions completely resolved. Only one non-target lesion remains 'just visible'. End of study CT scan continued to show sustained Partial Response.

Safety: Had slight allergic reaction to carboplatin, managed by steroids and anti-histamines.

Best Response Evaluation Criteria In Solid Tumors (RECIST) Response: Partial Response.

Best GCIG Response: Partial Response CA125 reduction 88% (218-27).

Patient 002

Diagnosis: Recurrent platinum refractory (PFI 0 months) stage IV, grade 3 serous papillary ovarian carcinoma. BRCA unknown.

Age 68 years, PS=0

Diagnosed in 2010. Presented in May 2010. Had suboptimal debulking surgery on 15 June 2010. Pre-treatment CA125 was 2,056.

1. December 2010: Completed 6 cycles of carboplatin+taxol.

2. August 2011-August 2012. Received carboplatin+paclitaxel+PDGFR inhibitor/placebo on MORAB Study followed by maintenance PDGFR inhibitor/placebo until evidence of disease progression.

3. March 2013: Completed 6 cycles of gemcitabine+carboplatin with a post-treatment CA125 of 441.

4. May-November 2013: Received 6 cycles of pazobanib+weekly paclitaxel followed by maintenance pazopanib until November (PAZPET Study).

5. June 2014 commenced carboplatin+caelyx but progressed after 4 Cycles.

Commenced on study on 2 Dec. 2014. NUC-1031 750 mg/m$^2$ and carboplatin AUC4, and has completed the study (6 Cycles).

Efficacy: CA125 rapidly rising at study entry with a baseline 865, but has had significant reduction in CA125 in this study. Per vaginal bleeding at baseline stopped following Cycle 1. CT scan on 10 Feb. 2015 showed Stable Disease to RECIST with a SLD reduction of 14%. End of Study CT scan showed sustained Stable Disease to RECIST.
Safety: Raised ALT following C1 D1 and treatment delayed for 1 week. C2 D8 delayed 1 week due to chest infection. C4 D8 omitted due to neutropaenia (G4). Required GCSF support.
Best RECIST Response: Stable Disease (14% reduction).
Best GCIG Response: Partial Response CA125 reduction 56% (865-377).
Patient 003
Diagnosis: Recurrent, platinum refractory (PFI 0 month) stage IIIb, grade 3 serous ovarian carcinoma. BRCA 1 and 2 mutations.
Age 37 years, PS=1
Diagnosed following primary debulking surgery on 16 Mar. 2010.
1. August 2010: Completed 6 Cycles of adjuvant carboplatin+paclitaxel.
2. February-August 2012: Received carboplatin+paclitaxel+PDGFR inhibitor/placebo (MORAB Study) followed by maintenance MORAB until progression.
3. September 2012-February 2013: Received daily pazopanib with weekly paclitaxel for 6 cycles followed by maintenance pazopanib in (PAZPET) study.
4. July 2013-April 2014: Received daily AKT inhibitor plus 3 weekly carboplatin+paclitaxel (AKTRES) study for 6 cycles followed by daily AKT inhibitor until disease progression.
5. June-October 2014: Received 4 cycles gemcitabine+carboplatin until disease progression, with bowel obstruction. Underwent colectomy and resection of adhesions and peritoneal disease.
6. November-December 2014: Received 2 cycles of liposomal doxorubicin, but discontinued due to disease progression.
Commenced on study 21 Jan. 2015. NUC-1031 750 mg/m$^2$ and carboplatin AUC4, received 1 Cycle. Dose reduced for C2 D1 to NUC-1031 500 mg/m$^2$ and carboplatin AUC3, and has now completed the Study.
Efficacy: CT Scan on 1 Apr. 2105 showed Stable Disease to RECIST with a SLD reduction of 5%. Significant reduction in CA125. End of Study CT scan showed Progressive Disease with a 50% increase in SLD from baseline.
Safety: Recurrent delays in treatment due to myelosuppression: max of G4 thrombocytopenia and G4 neutropenia. Required dose delays, dose reductions and GCSF. D8 was omitted from each Cycle from C2 onwards. Two hospital admissions due to infection.
Best RECIST Response: Stable Disease (5% reduction).
Best GCIG Response: Partial Response CA125 reduction 57% (272-117).
Patient 004
Diagnosis: Recurrent partially platinum sensitive (PFI 8 months) stage IV grade 3 serous adenocarcinoma of the right ovary. BRCA negative.
Age 64 years, PS=0
Diagnosed in May 2012 following identification of a pelvic mass and multiple liver metastases during investigations for abdominal pain. CT guided liver biopsy revealed grade 3 serous adenocarcinoma (ER+).
1. May-November 2012: Received 6 Cycles of carboplatin+paclitaxel+bevacizumab (3 weekly) but considered to have inoperable disease by local oncologists.
Self-referred for liver ablation which was administered in January 2013 and had a second opinion regarding operability. Underwent delayed primary debulking surgery in February 2013, which was followed by 3 Cycles of carboplatin+paclitaxel+bevacizumab, completed in May 2013. Continued on maintenance bevacizumab until October 2013.
2. November 2013-May 2014: Received 6 Cycles of carboplatin+caelyx (had one treatment delay due to neutropaenia), leaving only intrahepatic disease.
3. August 2014: Underwent Y-90 radio-embolisation (Sirtex) to both liver lobes. January 2015: CT scan showed disease progression with liver and peritoneum metastases, and rapidly rising CA125 levels.
Commenced on study 3 Feb. 2015. NUC-1031 750 mg/m$^2$ and carboplatin AUC5 received 1 dose. Reduced to AUC4 from C2 D1 and received 1 Cycle. NUC-1031 reduced to 500 mg/m$^2$ for C3 D1 and has completed 2 further Cycles. Carboplatin reduced to AUC3 for Cycle 5, received 1 dose.
Efficacy: PET scan on 24 Feb. 2015 showed good metabolic response and slight reduction in tumour volume. CT Scan on 8 April 2015 showed Stable Disease to RECIST with a SLD reduction of 22%. Significant reduction in CA125. Patient reported that she is no longer able to feel tumour nodules on her liver and has had significant reduction in pain around primary tumour site following C1. CT scan on 13/5 showed Progressive Disease with new lesions.
Safety: Recurrent neutropaenia and thrombocytopaenia requiring dose delays, dose reductions and GCSF. LFTs persistently elevated due to liver metastases.
Best RECIST Response: Stable Disease (22% reduction).
Best GCIG Response: Partial Response CA125 reduction 77% (1,574-356).
Patient 005
Diagnosis: Recurrent, platinum-resistant (PFI 3 months) stage IV grade 3 bilateral serous adenocarcinoma of the ovary. BRCA status unknown.
Age 75 years, PS=1
Diagnosed in December 2011 and underwent total abdominal hysterectomy, bilateral salpingo-oophorectomy and omentectomy.
1. May 2012: Completed 6 adjuvant cycles of carboplatin+paclitaxel.
2. June-December 2013: Received 6 Cycles of carboplatin+caelyx on chemotherapy arm of DESKTOP study.
3. July 2014-January 2015: Received 3 weekly carboplatin and paclitaxel with daily AKT inhibitor followed by maintenance AKT inhibitor until PD on AKTRES study.
Commenced on study 20 Feb. 2015. NUC-1031 750 mg/m$^2$ and carboplatin AUC4 and has completed the Study.
Efficacy: End of C3 CT scan showed Stable Disease to RECIST with a SLD reduction of 26%. Significant reduction in CA125. End of Study CT scan showed sustained Stable Disease to RECIST.
Safety: C2 D1 delayed for due to neutropaenia (G3). One hospital admission due to infection. Fatigue (G1).
Best RECIST Response: Stable Disease (26% reduction).
Best GCIG Response: Partial Response CA125 reduction 80% (638-127).
Patient 006
Diagnosis: Recurrent, platinum-refractory (PFI 0 months) stage IIIc grade 3 serous adenocarcinoma of the ovary. BRCA status unknown.
Age 70 years, PS=1
Diagnosed in September 2012. Underwent supra-radical surgery in 4 Oct. 2012, leaving residual disease.
1. March 2013: Completed 6 Cycles of carboplatin.
2. November 2013-April 2014: Received 6 cycles weekly paclitaxel.

3. July 2014-September 2014: Received 3 Cycles of carboplatin+gemcitabine but with progressive disease.
Commenced on Study 20 Feb. 2015. NUC-1031 750 mg/m$^2$ and carboplatin AUC4 and has completed 4 Cycles to date. NUC-1031 dose reduced to 500 mg/m2 and AUC4 for C5 D1 and has completed one further Cycle.
Efficacy: Post C3 CT scan showed Stable Disease to RECIST with a SLD reduction of 28%. Significant reduction in CA125, now normal from a baseline of 48.
Safety: C2 D1 delayed for 3 days due to neutropaenia (G2). Pain increasing, but mainly due to low compliance of opiods. One hospital admission due to chest infection.
Was admitted for surgery to a strangulated hernia. Will receive and of Study CT scan on recovery.
Best Response: Stable Disease (28% reduction).
Best GCIG Response: Stable Disease CA125 reduction 48% (48-25).

Patient 007
Diagnosis: Recurrent, platinum-sensitive (PFI 14 months), Stage lib large cell neuroendocrine tumour of ovarian origin. BRCA unknown; non-CA125 expressor
Age 77 years, PS=1
Diagnosed in November 2011. Had debulking surgery with no residual disease.
1. March 2012: Completed 6 cycles of adjuvant carboplatin+etoposide.
2. July-November 2013: Completed 6 Cycles of 3 weekly carboplatin+paclitaxel to CR. January 2015: CT scan showed progressive nodal disease.
Commenced on Study 25 Feb. 2015. NUC-1031 750 mg/m$^2$ and carboplatin AUC4, and has completed 4 Cycles to date.
Efficacy: Post C3 CT scan showed Partial Response to RECIST with an SLD reduction of 50%. End of Study CT scan showed a Complete Response to RECIST with the disappearance of all target and non-target lesions.
Safety: C2 D1 delayed for 3 days due to neutropaenia (G2). Constipation G2 (associated with anti-emetic). Following C4 admitted with neutropaenia G4 and line infection. Dose reduced to for Cycle 5.
Best RECIST Response: Complete Response.
Non expressor of CA125.

Patient 008
Diagnosis: Recurrent, partially platinum sensitive (PFI 7 months) stage IIIc grade 3 serous adenocarcinoma of ovary. BRCA status unknown.
Age 54 years, PS=0
Diagnosed with non-debulked stage IIIc grade 3 serous adenocarcinoma of ovary following laparoscopic biopsy performed on 27 Mar. 2012.
1. September 2012: Completed six cycles of carboplatin+paclitaxel on the ICON8 study, but disease still inoperable.
2. May 2014: Commenced carboplatin, gemcitabine and bevacizumab, but only received one cycle before declining further chemotherapy.
February 2015: Returned with symptomatic progression, CT-progressive peritoneal disease, and rapidly rising CA125.
Commenced on Study 10 Mar. 2015. NUC-1031 500 mg/m$^2$ and carboplatin AUC5 and has completed 3 Cycles to date. Carboplatin reduced to AUC4 for Cycle 4 and has received 2 more Cycles.
Efficacy: Post C3 CT scan showed Stable Disease to RECIST with a SLD reduction of 15%. Significant reduction in CA125. End of Study CT scan showed sustained Stable Disease with an SLD reduction of 28%.
Safety: Fatigue (G1). C3 D8 omitted due to neutropaenia (G2). Reduced to AUC4 for Cycle 4.
Best RECIST Response: Stable Disease (28% reduction).
BEST GCIG Response: Partial Response CA125 reduction 97% (791-23).

Patient 009
Diagnosis: Recurrent, platinum resistant (PFI 4 months) stage IV grade 3 serous adenocarcinoma of the ovary. BRCA1 mutation.
Age 63 years, PS=0
Diagnosed following ultrasound guided biopsy on 7 Dec. 2012.
1. January 2013: Received neo-adjuvant carboplatin+paclitaxel on the ICON 8 study and post cycle 3 underwent delayed primary debulking surgery on 26 Feb. 2013. Surgery was ultra-radical and included anterior resection of the rectum, splenectomy, peritoneal stripping and lymph node dissection. Completed 4 Cycles of post-op chemotherapy with carboplatin and docetaxel (because of paclitaxel allergy).
2. May 2014: Received carboplatin, gemcitabine and P53-targeting agent (APR-243) in PISARRO study, with Partial Response.
February 2015: disease recurrence.
Commenced on Study 13 Mar. 2015. NUC-1031 500 mg/m$^2$ and carboplatin AUC5, has completed 4 Cycles. Carboplatin reduced to AUC4 for C5.
Efficacy: Post C3 CT scan showed Stable Disease to RECIST with a SLD reduction of 2%. Significant reduction in CA125. End of Study CT Scan showed sustained Stable Disease to RECIST.
Safety: Fatigue G1 (baseline G1). Presented for C4 D8 with neutropaenia, G2. D8 omitted and carboplatin reduced to AUC4.
Best RECIST Response: Stable Disease (2% reduction).
Best GCIG Response: Stable Disease CA125 reduction 44% (75-42).

Patient 010
Diagnosis: Recurrent, platinum resistant (PFI 5 months) stage 3c, grade 3 serous carcinoma of the ovary.
Age 76 years, PS=1
Diagnosed in February 2013 and had right salpingo-oophrectomy and omentectomy performed, leaving sub-centimetre deposits of residual peritoneal disease. Pre-treatment CA125 level was 930.
1. April-August 2013 completed 6 Cycles of carboplatin and taxol within arm 3 of ICON 8 study.
2. Asymptomatic rise in CA125 in February 2014. June 2014 commenced gemcitabine+carboplatin+bevacizumab.
3. Commenced maintenance bevacizumab November 2014. Stopped March 2015 due to rising CA125.
Commenced on Study 15 Apr. 2015. NUC-1031 500 mg/m$^2$ and carboplatin AUC5, has completed 4 Cycles.
Efficacy: Post C3 CT scan showed Stable Disease to RECIST. CA125 has increased from 304 at baseline to 515 at end of Cycle 3. End of Study CT scan showed sustained Stable Disease to RECIST.
Safety: Tolerated treatment well
Best RECIST Response: Stable Disease.
Best GCIG Response:

Example 3—Pharmacokinetic Analysis of dFdCTP Concentrations from the PRO-002 Clinical Study (NUC-1031 in Combination with Carboplatin) and Comparison with Results from the ProGem1 Clinical Study (NUC-1031 Alone)

Materials and Methods
1. Materials
dFdCTP reference compound was obtained from Biorbyt, UK. Lymphoprep from STEMCELL Technologies Inc., UK.

Perchloric acid (PCA), ammonium acetate (NH4Ac) and ammonia were all obtained from Sigma Aldrich, UK. LC-MS grade Water, methanol, acetonitrile and formic acid were all obtained from Fisher Scientific, UK.

2. Methods

A. Blood Collection and PBMCs Preparation:

6 ml of blood was collected using heparinised blood collection tubes. After centrifugation and separation of plasma, buffycoat was collected and transferred to new test tube containing 3 ml of Lymphoprep density gradient. After centrifugation, the upper interface containing the PBMC layer was transferred to new test tube. After washing with phosphate buffered saline (PBS), PBMCs were re-suspended in 100 μl PBS. Then, another 100 μl of 0.8 M PCA was added and the mixture was vortex mixed and centrifuged followed by transfer of 100 μl supernatant to new test tube. The PCA extracts were stored at −80° C. until time of analysis.

B. Sample Extraction (PBMCs):

PCA extracts were buffered using 50 μl of 1M NH4Ac, then neutralised using 20 μl of 10% ammonia solution. Finally, 5 μl containing the internal standard 8-ChloroATP and 5 μl deionised water were then added. The extracts were transferred to LC-MS vials and 10 μl were injected into the UPLC-MS/MS system.

3. Chromatography Method and Sample Analysis 10 mg/mL stock solution of the analyte was prepared and aliquot frozen at −80° C. until use. The analyte was resolved using an ultra-performance liquid chromatography system (Accela UPLC, Thermo Scientific, UK) equipped with a Biobasic AX, 5 μm, 50×2.1 mm column (Thermo Electron Corporation, Murrieta, Calif., USA) and a mobile phase consisting of a mixture of 10 mM NH4Ac in ACN/H2O (30:70 v/v), pH 6.0 (A), and 1 mM NH4Ac in ACN/H2O (30:70 v/v), pH 10.5 (B). The mobile phase gradient was employed, comprising: buffer A=95% at 0-0.5 min, from 95 to 0% over 1.25 minutes, held at 0% for 1.75 minute, from 0 to 95% over 0.1 minutes, ending with 95% for 2.9 minutes, all at a flow rate of 500 μl/min.

4. Mass Spectrometry Method

Eluting compounds of interest were detected using a triple stage quadrupole Vantage mass spectrometry system (Thermo Scientific, UK) equipped with an electrospray ion source. Samples were analyzed in the Multiple Reaction Monitoring (MRM), positive (+ve) and negative (−ve) ion modes at a spray voltage of 3500 and 3000 V, respectively. Nitrogen was used as sheath and auxiliary gases at a flow rate of 50 and 20 arbitrary units, respectively. Argon was used as collision gas with pressure of 1.5 mTorr.

Results

Figure 2:
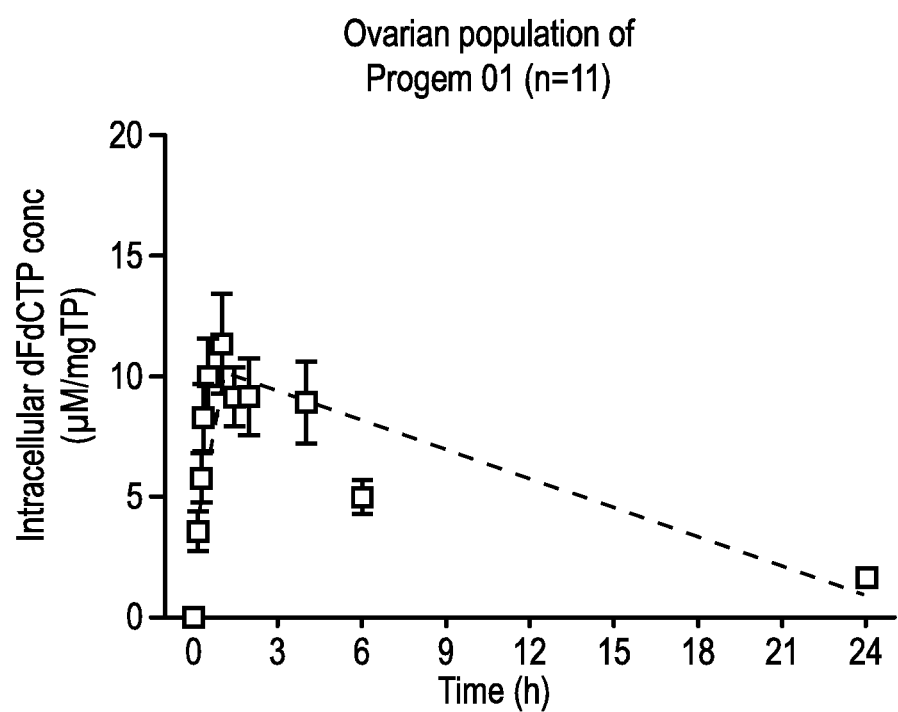
FIG. 2 shows PK time concentration curve for intracellular dFdCTP in PBMCs after intravenous administration of NUC-1031 cycle 1 day 1 (n=11). Intracellular concentrations were normalised to tissue protein concentrations. dFdCTP=2',2'-difluoro-2'-deoxycytidine; PBMCs=Peripheral Blood Mononuclear Cells.

NUC-1031 single agent caused rapid and prolonged intracellular accumulation of the active metabolite difluorodeoxycytidine triphosphate (dFdCTP) with a dFdCTP maximum concentration ($C_{max}$) of 11.3 μM/mg tissue protein (TP) at $T_{max}$ of 1 hour End Of Infusion (EOI) and an apparent $t_{1/2}$ of 9.6 hours. These data show the ability of NUC-1031 to deliver very high and sustained levels of the active anti-cancer metabolite dFdCTP. Intracellular Area Under the concentration Curve (AUC) for dFdCTP was 103.3 μM/mgTP·hr for the first 24 hours EOI (FIG. 2).

Figure 3:
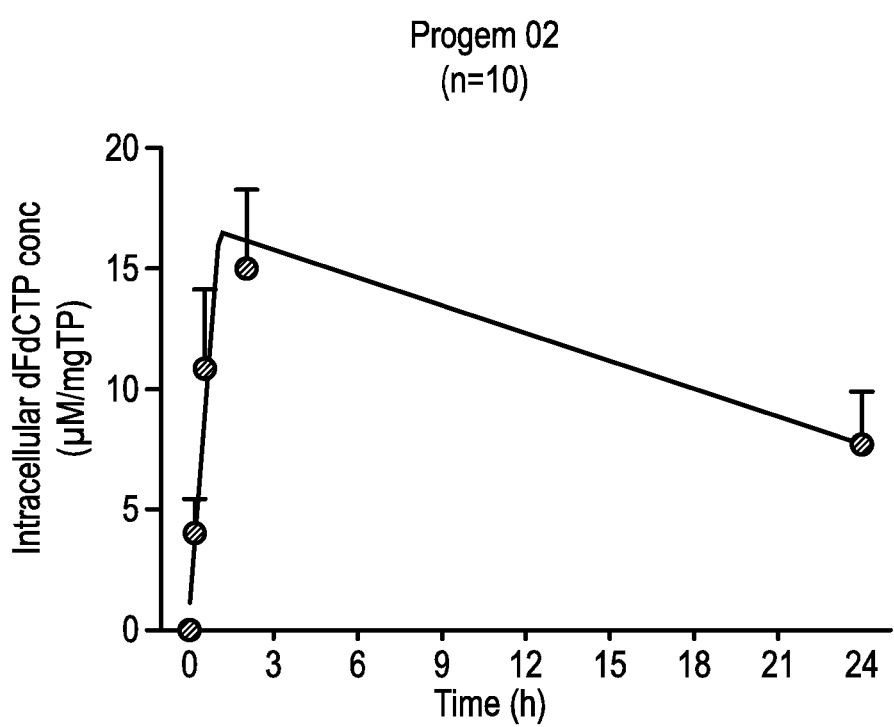
FIG. 3 shows PK time concentration curve for intracellular dFdCTP in PBMCs after intravenous administration of NUC-1031 and carboplatin cycle 1 day 1 (n=10). Intracellular concentrations were normalised to tissue protein concentrations. dFdCTP=2',2'-difluoro-2'-deoxycytidine; PBMCs=Peripheral Blood Mononuclear Cells.
Figure 4:
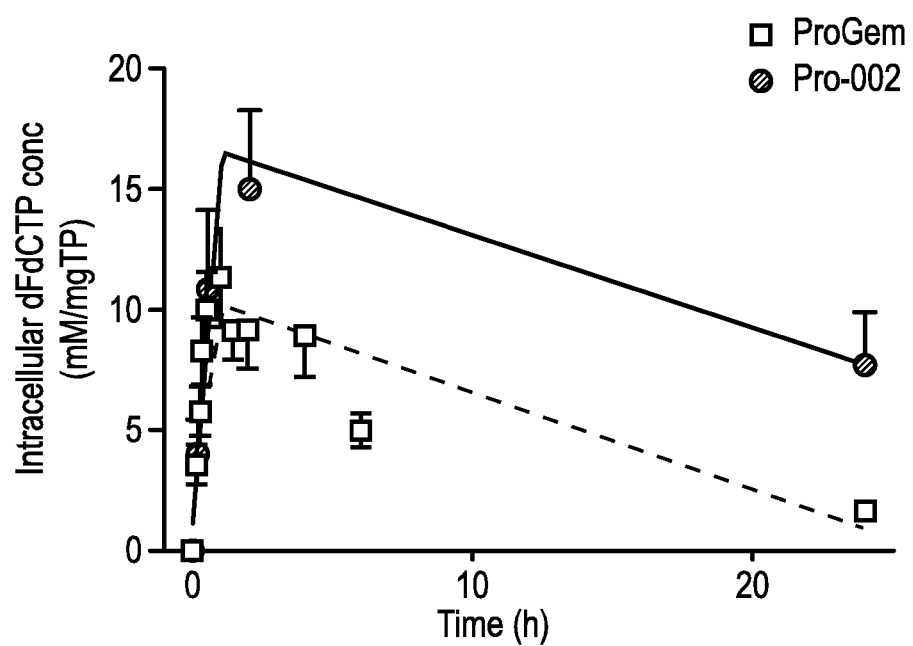
FIG. 4 shows overlay of the PK time concentration curves for intracellular dFdCTP in PBMCs after intravenous administration of single agent NUC-1031 and the combination regimen NUC-1031 and carboplatin cycle 1 day 1. Intracellular concentrations were normalised to tissue protein concentrations. dFdCTP=2',2'-difluoro-2'-deoxycytidine; PBMCs=Peripheral Blood Mononuclear Cells.

The combination regimen NUC-1031 with carboplatin was administered to 10 patients with ovarian cancer as part of the Phase Ib study PRO-002. The intracellular dFdCTP $C_{max}$ reached 15.1 μM/mgTP and the AUC was 235.0 μM/mgTP·hr for the first 24 hours EOI (FIG. 3). The mean pharmacokinetic parameters normalised to 500 mg/m² gemcitabine dose are displayed in the table below and compared with the data obtained in the ProGem1 patients with ovarian cancer exposed to single agent NUC-1031.

TABLE 4

Mean PK parameters comparison of ProGem1 and PRO-002 studies
Mean PK Parameters (normalized to 500 mg/m² gemcitabine dose)

| | ProGem1 (n = 11) (NUC-1031 as a single agent) | PRO-002 (n = 10) (NUC-1031 in combination with carboplatin) |
|---|---|---|
| $C_{max}$ (μM/mgTP) | 11.3 | 15.1 |
| $T_{max}$ (hr) | 1 | 2 |
| $AUC_{0-24}$ (μM/mgTP · hr) | 103.3 | 235 |
| Apparent $t_{1/2}$ (hr) | 9.6 | 20.3 |
| Clearance (L/hr) | 3.9 | 1.2 |

DISCUSSION

Pharmacokinetics of NUC-1031 single agent (ProGem1) were very favourable, achieving intracellular dFdCTP $C_{max}$ concentrations around 10× higher than those observed with gemcitabine. Combination regimen NUC-1031 with carboplatin (PRO-002) showed a 34% intracellular dFdCTP $C_{max}$ increase and a 127% $AUC_{0-24}$ increase over single agent use. The synergy observed in the dFdCTP levels following NUC-1031 with carboplatin treatment has significant potential clinical implications, including broader clinical utility to treat cancers where high intracellular dFdCTP levels are required to block tumour growth and in treating recurrent cancers following single agent use.

The invention claimed is:

1. A method of treating cancer, the method comprising administering to a subject in need thereof a therapeutically effective amount of a compound of Formula 2:

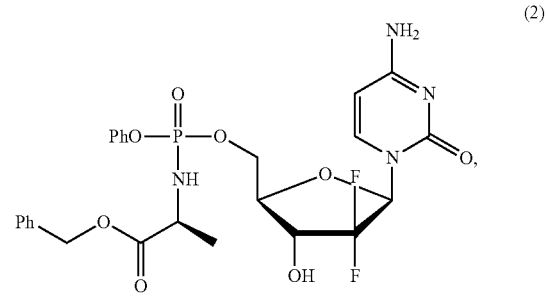 [SMILES: C[C@H](NP(=O)(OC[C@H]1O[C@@H](n2ccc(N)nc2=O)C(F)(F)[C@H]1O)Oc1ccccc1)C(=O)OCc1ccccc1]

or a pharmaceutically acceptable salt thereof, in combination with carboplatin; wherein the cancer is ovarian cancer.

2. The method of claim 1, wherein the compound of Formula 2 comprises greater than about 90% of the diastereomer represented by Formula 3:

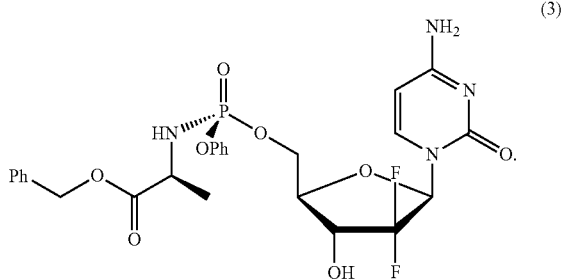 [SMILES: C[C@H](N[P@](=O)(OC[C@H]1O[C@@H](n2ccc(N)nc2=O)C(F)(F)[C@H]1O)Oc1ccccc1)C(=O)OCc1ccccc1]

(3)

3. The method of claim 1, wherein the compound of Formula 2 is a mixture of phosphate diastereoisomers.

4. The method of claim 1, wherein the compound of Formula 2 is not in the form of a salt.

5. The method of claim 1, wherein the compound of Formula 2 is administered intravenously.

6. The method of claim 1, wherein the cancer is relapsed.

7. The method of claim 1, wherein the cancer is refractory, resistant or partially resistant to carboplatin.

8. The method of claim 1, wherein the cancer is sensitive to carboplatin.

9. The method of claim 1, wherein the dose of the compound of Formula 2, or a pharmaceutically acceptable salt thereof administered at each administration event is between 250 mg/m$^2$ and 1250 mg/m$^2$.

10. The method of claim 1, wherein at each administration event the compound of Formula 2, or a pharmaceutically acceptable salt thereof, is administered in a dosage between 300 mg/m$^2$ and 1000 mg/m$^2$.

11. The method of claim 1, wherein at each administration event the compound of Formula 2, or a pharmaceutically acceptable salt thereof, is administered in a dosage between 400 mg/m$^2$ and 800 mg/m$^2$.

12. The method of claim 1, wherein at each administration event carboplatin is administered in a dosage selected to provide an AUC of between 2 and 5.5 mgmL$^{-1}$ min$^{-1}$.

13. The method of claim 1, wherein at each administration event carboplatin is administered in a dosage selected to provide an AUC of between 2.5 and 4.5 mgmL$^{-1}$ min$^{-1}$.

14. The method of claim 1, wherein the compound of Formula 2, or a pharmaceutically acceptable salt thereof, and carboplatin are administered simultaneously.

15. The method of claim 1, wherein the compound of Formula 2, or a pharmaceutically acceptable salt thereof, are administered sequentially.

* * * * *